US010292953B2

(12) United States Patent
Martinez-Alzamora et al.

(10) Patent No.: US 10,292,953 B2
(45) Date of Patent: May 21, 2019

(54) PHARMACEUTICAL COMPOSITION OF IBUPROFEN AND TRAMADOL FOR OPHTHALMIC USE

(71) Applicant: Farmalider, S.A., Alcobendas (Madrid) (ES)

(72) Inventors: Fernando Martinez-Alzamora, Alcobendas (ES); Jose Miguel Rizo Martinez, Alcobendas (ES); Antonia Gomez Calvo, Alcobendas (ES); Nuria Sanz Menendez, Alcobendas (ES); Angel Munoz Ruiz, Alcobendas (ES)

(*) Notice: Subject to any disclaimer, the term of this patent is extended or adjusted under 35 U.S.C. 154(b) by 0 days.

(21) Appl. No.: 14/511,321

(22) Filed: Oct. 10, 2014

(65) Prior Publication Data

US 2015/0105468 A1    Apr. 16, 2015

(30) Foreign Application Priority Data

Oct. 11, 2013    (ES) .................. 2013000963

(51) Int. Cl.
*A61K 9/00* (2006.01)
*A61K 31/135* (2006.01)
*A61K 31/192* (2006.01)
*A61K 47/18* (2017.01)
*A61K 47/02* (2006.01)

(52) U.S. Cl.
CPC .......... *A61K 31/192* (2013.01); *A61K 9/0048* (2013.01); *A61K 31/135* (2013.01); *A61K 47/02* (2013.01); *A61K 47/183* (2013.01)

(58) Field of Classification Search
CPC .. A61K 9/0048; A61K 31/135; A61K 31/137; A61K 31/192

USPC .................................................. 514/568, 741
See application file for complete search history.

(56) References Cited

U.S. PATENT DOCUMENTS

2004/0224010 A1* 11/2004 Hofland ................. A61K 9/127
424/450

FOREIGN PATENT DOCUMENTS

| CN | 1513442 A | * | 7/2004 | ........... A61K 31/198 |
| CN | 1513442 A | * | 7/2004 | |
| CN | 1513442 A | * | 7/2004 | ........... A61K 9/0048 |
| EP | 0546676 A1 | * | 6/1993 | ............. A61K 31/19 |
| EP | 0546676 A1 | * | 6/1993 | ............. A61K 31/19 |
| EP | 0546676 B1 | * | 12/2004 | ............. A61K 31/19 |
| WO | WO 2012136969 A2 | * | 10/2012 | ........... A61K 9/0048 |
| WO | WO-2012136969 A2 | * | 10/2012 | ........... A61K 9/0048 |

OTHER PUBLICATIONS

Chou et al (Pharmacological Reviews vol. 58 pp. 621-681. Published 2006.*

* cited by examiner

*Primary Examiner* — Theodore R. West
*Assistant Examiner* — George W Kosturko
(74) *Attorney, Agent, or Firm* — Cook Alex Ltd.

(57) ABSTRACT

The present invention relates to a pharmaceutical composition of ibuprofen and tramadol for ophthalmic use. Said composition is effective and safe for the treatment of ocular inflammation and/or pain associated to different diseases or pathological states which affect the eye area In particular, the ophthalmic composition of the invention is indicated, for example, for the treatment of pain and/or inflammation after eye surgery.

11 Claims, No Drawings

PHARMACEUTICAL COMPOSITION OF IBUPROFEN AND TRAMADOL FOR OPHTHALMIC USE

FIELD OF THE INVENTION

The present invention relates to a pharmaceutical composition for its administrative by ophthalmic route which contains a combination of ibuprofen and tramadol as active principles.

STATE OF THE PRIOR ART

There are numerous pathological states which specifically affect the eye area and which present pain or inflammation.

Thus, various ocular inflammatory disorders can be mentioned which may affect any part of the eye or the surrounding tissues such as scleritis, episcleritis, blepharitis, retinitis, keratitis, conjunctivitis or uveitis, among others; or pain and inflammation may also be presented as a consequence of traumatic lesions in the eye area, and also as a consequence of ophthalmic surgery.

In particular, post-surgical states are typical after ophthalmic surgery, for example, after cataract surgery or refractive surgery, wherein the patient has symptoms of ocular inflammation and pain.

The topical administration of drugs is the preferred route for the treatment of ocular inflammation and pain, since it provides a greater concentration of the drug locally in the affected area, whilst avoiding the undesired systemic effects associated with oral administration.

Among the various drugs suitable for being used by ophthalmic route for the treatment of pain and inflammation we can highlight the non-steroidal anti-inflammatory drugs (NSAIDs), which act by the inhibition of the cyclooxygenase (COX) enzyme, in its isotherms COX-1 and COX-2, and the subsequent inhibition of prostaglandin formation, which are important mediators of the inflammatory response, in particular also of intraocular inflammation.

NSAIDs have been in widespread use in ophthalmology, as described, for example, in the review article of Kim et al. *Nonsteroidal Anti-inflammatory drugs in ophthalmology*, Survey Ophthalmol., 2010, 55 (2), p. 108-133, highlighting the use of NSAIDs in topical form, e.g. to reduce myosis and inflammation in eye surgery, for the treatment of scleritis, prevention and treatment of macular edema associated with cataract surgery, to alleviate post-operative pain and photophobia associated with refractive surgery and to reduce the itching associated with allergic conjunctivitis.

Thus, various eyedrops have been marketed based on NSAIDs as active principles, mainly with bromfenac, diclofenac, flurbiprofen, ketorolac and nepafenac. It should be observed that, despite the fact that ibuprofen is a significant member of the family of the NSAIDs, and that it is habitually used by oral route as an analgesic and antipyretic agent, there are, in contrast, few references to its topical ophthalmic use.

Furthermore, despite the therapeutic efficacy demonstrated by eyedrops based on NSAIDs, their use is not free from the risk of certain undesired effects.

In particular, in reference to ibuprofen, the article Baydounet al. *Comparison of different ibuprofen-amino acid compounds with respect to emulsifying and cytotoxic properties*. Int. J. Pharm., 2004, 274 (1-2), p. 157-65, describes how a solution of ibuprofen in the form of salt with lysine or with arginine adversely affected the integrity of the cornea, according to an in vitro study performed with porcine cornea.

In general, the most frequent adverse affect of eyedrops based on NSAIDs are generally mild, of the type of ocular burning, conjunctival hyperaemia or hypersensitivity reactions.

In some cases, however, when the patients are treated with high doses or during prolonged periods of time, the use of topical NSAIDs may cause more serious complications, mainly keratitis, corneal thinning, corneal erosions, corneal ulcerations and corneal perforations, as described, for example, in the article Guideraet al. *Keratitis, ulceration, and perforation associated with topical nonsteroidal anti-inflammatory drugs*. Ophthalmology 2001, 108 (5), p. 936-44.

In light of this, it is evident that it would be desirable to have therapeutic strategies alternative to the use of topical NSAIDs for the treatment of ocular pain and inflammation, which involve a lower risk for the patient.

Other drugs described in the state of the art for their topical use in the treatment of ophthalmic pain are, for example, local anaesthesia, such as tetracaine, procaine benoxinate or proparacaine, however these products are also subject to certain risks, so that their repeated or extended use is associated with damaging effects for the corneal epithelium and on occasions may case more serious toxic effects, such as corneal infiltration, ulceration or even corneal perforation, as described in the article McGee et al. *Toxicities of topical ophthalmic anesthetics*. Review. Expert Opin. Drug Safety, 2007, 6 (6), p. 637-640.

Alternatively, the use of opioid substances has also been described for topical ocular use for the local treatment of pain. Thus, for example, in the article Faktorovichet al. *Effect of topical 0.5% morphine on postoperative pain after photorefractive keratectomy*. J. Refract. Surg., 2010, 26 (12), p. 934-41 the use is described of an ophthalmic composition of 0.5% morphine as analgesic in patients who have undergone photorefractive keratectomy (PRK).

However, in a later study it was observed that an aqueous solution of 1% morphine did not demonstrate analgesic effects in the treatment of corneal pain in dogs and cats, as described in the article Thomson et al. *Preliminary investigations into the analgesic effects of topical ocular 1% morphine solution in dogs and cats*. Vet. Anaesth. Analg., 2013 Jul. 6, doi: 10.1111/vaa.12069.

Furthermore, it should be highlighted that other drugs belonging to the family of the opioids were ineffective by ophthalmic route. Thus, fentanyl did not show activity as analgesic when it was applied by ocular route in patients with corneal erosion as a consequence of surgical intervention, as described in the article Zollneret al. *Topical fentanyl in a randomized, double blind study in patients with corneal damage*. Clin. J. Pain, 2008, 24 (8), p. 690-696.

Neither did the opioid semi-synthetic nalbuphine applied in the form of 1% topical solution demonstrate analgesic efficacy in an experimental test performed on rabbits which had ulceration of the cornea as described in the article Ladino Silva et al. *Topical 1% nalbuphine on corneal sensitivity and epitheilization after experimental lamellar keratectomy in rabbits*. Ciencia Rural, 2012, 42 (4), p. 679-684.

In conclusion, despite the need to find an effective and safe alternative for the local treatment of pain and ocular inflammation, currently the state of the art does not provide a suitable solution to said problem.

Thus, there is still the need to have a composition for topical ophthalmic use for the treatment of ocular inflammation and pain, which is stable and therapeutically effective, and also safe and involves a lower risk of secondary effects with respect to the currently available medicines, in particular, NSAIDs.

OBJECT OF THE INVENTION

The object of the present invention is an ophthalmic pharmaceutical composition comprising ibuprofen and tramadol.

Part of the object of the invention is also the use of a combination of ibuprofen and tramadol for the preparation of an ophthalmic pharmaceutical composition for the treatment of ocular inflammation and/or pain.

DETAILED DESCRIPTION OF THE INVENTION

The object of the present invention is an aqueous ophthalmic pharmaceutical composition comprising:
a) ibuprofen, or a pharmaceutically acceptable salt thereof, in a concentration comprised between 0.01% (w/v) and 0.5% (w/v), preferably comprised between 0.05% (w/v) and 0.2% (w/v), more preferably comprised between 0.075% (w/v) and 0.14% (w/v), and even more preferably in a concentration of approximately 0.1% (w/v); and
b) tramadol or a pharmaceutically acceptable salt thereof, in a concentration, expressed as equivalent concentration of tramadol hydrochloride, comprised between 0.05% (w/v) and 2% (w/v), preferably comprised between 0.075% (w/v) and 1.5% (w/v), and, even more preferably in a concentration of approximately 0.1% (w/v) to 1.0% (w/v).

Thus, the authors of the present invention have developed a pharmaceutical composition for ophthalmic use consisting of the combination of ibuprofen and tramadol as active principles which are surprisingly effective for the treatment of ocular pain and inflammation and which also has the advantage of not causing the adverse effects described, frequently associated to the eye formulations of NSAIDs.

Ibuprofen

Ibuprofen is the International Nonproprietary Name (INN) by which (RS)-2-(4-isobutylphenyl)propionic acid is habitually known.

Ibuprofen is a drug belonging to the group of non-steroidal anti-inflammatory drugs (commonly called NSAIDs) which has analgesic, antipyretic and anti-inflammatory activity.

Ibuprofen was originally described in the 1960s in a family of patents of the company BootsPureDrug Co Ltd (e.g. in the British patent GB-A-971700, or in its North American equivalent U.S. Pat. No. 3,385,886), and it is currently a frequently used drug, so that for some years now numerous proprietary medicinal products have been marketed based on ibuprofen, mainly for their oral administration, and also occasionally for their administration by injection and by transcutaneous topical route.

It is known that the active enantiomer of ibuprofen is the (S) form, although it has been verified that mammals have an isomerase capable of converting the (R) form into active form (S).

Within the context of the present invention, the term ibuprofen includes ibuprofen in its racemic form ((R,S)-ibuprofen), the enantiomer (S) of ibuprofen ((S)-ibuprofen) and a mixture of the enantiomers (R) and (S) of ibuprofen in any proportion, preferably enriched in the (S) form. Preferably, the ibuprofen used in the compositions of the invention is selected from among (R,S)-ibuprofen and (S)-ibuprofen. More preferably, the compositions of the invention contain (R,S)-ibuprofen.

Ibuprofen is freely available commercially and it can also be prepared, for example, according to the process described in the aforementioned British patent application, GB-A-971700. The resolution of ibuprofen in its enantiomers is described, for example, in the article Brushan et al. *Resolution of enantiomers of ibuprofen by liquid chromatography: a review*, Biomed. Chromatogr., 1998, 12 (6), p 309.

Within the framework of the present invention, ibuprofen may be in its free acid form or in the form of a pharmaceutically acceptable salt. The pharmaceutically acceptable salts of ibuprofen include, for example, the salt with arginine (or ibuprofen arginate), the salt with lysine (or ibuprofen lysine), the salt with histidine, the sodium, salt and the potassium salt.

When the ibuprofen is in the form of ibuprofen arginate, the ophthalmic composition according to the invention may be prepared from ibuprofen and arginine separately and, in the aqueous medium of said composition, ibuprofen arginate is substantially formed. This allows that the ibuprofen and the arginine are not in a stoichiometrically fixed molar ratio 1:1 as would occur in the case of the previously prepared salt.

Thus, within the framework of the present invention, the term ibuprofen arginate, or ibuprofen in the form of salt with arginine, is used to indicate that the composition of the invention contains ibuprofen together with arginine, in any molar ratio.

Similarly, the salts with lysine and histidine are also understood in a broad form, so that said terms are used to indicate that the composition contains ibuprofen together with lysine or histidine, respectively, in any molar ratio.

In a preferred embodiment of the invention, ibuprofen is in the form of salt with arginine, which is typically called ibuprofen arginate.

In a more preferred embodiment of the invention, the ibuprofen is in the form of salt with arginine, wherein the molar ratio between ibuprofen:arginine is comprised between 1.2:1 and 1:1.2, more preferably comprised between 1:1 and 1:1.2, and even more preferably comprised between 1:1.05 and 1:1.1.

In an alternative embodiment of the invention, ibuprofen arginate is incorporated in the form of a previously formed salt (therefore, with a molar ratio 1:1).

Said salt can be prepared, for example, as described in the Spanish patent application ES435416.

Arginine, for its part, is an α-amino acid, which is found in nature in its enantiomeric form L. In the context of this invention, arginine is understood as any of its enantiomeric forms: L-arginine, D-arginine and its mixtures. Preferably, arginine is in the form of L-arginine.

Arginine can be commercially obtained from different sources.

Preferably the concentration of ibuprofen in the ophthalmic pharmaceutical composition of the invention is comprised between 0.01% and 0.5%, more preferably comprised between 0.05% and 0.2%, even more preferably comprised between 0.075% and 0.14%, and even more preferably, the ibuprofen is in a concentration of approximately 0.1%.

Throughout the present description, the concentrations of the components of the composition expressed as per cent (%) also relate, unless stated otherwise, to the percentage expressed in weight/volume, which can be symbolized as "% (w/v)", and which indicate the weight of each component in grams per 100 ml of composition.

Within the context of the present invention, the term "approximately" before a certain value indicates that there is a slight margin of variation for the indicated value, which is considered more or less 5% of said value.

Throughout the present description, the concentrations of ibuprofen in the ophthalmic composition of the invention, always relate to the concentration of ibuprofen in its acid form, irrespective of whether a salt thereof is used, for example, the salt with arginine, for the preparation of the composition.

Tramadol

Tramadol is the International Nonproprietary Name (INN) by which the compound (±)-cis-2-[(dimethylamino) methyl]-1-(3-methoxyphenyl)-cyclohexanol is known.

Tramadol is a drug belonging to the group of the opioids, although its mechanism of action is usually classified as an "atypical" opioid since it is neither completely opioid nor completely non-opioid. Tramadol has a dual action mechanism since, on the one hand, it acts on the μ-opioid receptors to which it bonds with low affinity, and on the other, it inhibits the recapturing of noradrenaline and serotonine, so that it increases the concentration of these neurotransmitters in localized areas of the brain, decreasing the pain threshold, as described, for example, in the article Raffa et al. *Opioid and nonopioid components independently contribute to the mechanism of action of tramadol, an atypical' opioid analgesic*, J. Pharmacol. Exp. Ther., 1992, 260 (1), p 275-85.

Tramadol is commercially distributed and can be prepared, for example, according to the process described in the U.S. Pat. No. 3,652,589.

In the context of the present invention, the term tramadol includes, in a broad sense, any of its solvates, polymorphs, stereoisomers, mixtures of stereoisomers and racemic forms.

Pharmaceutically acceptable salts of tramadol relate to the addition salts with acids, which can be prepared according to conventional methods well known by a person skilled in the art, using pharmaceutically acceptable substantially non-toxic organic or inorganic and acids. Said acids include hydrochloric acid, nitric acid, phosphoric acid, acetic acid, propionic acid, malonic acid, succinic acid, citric acid, tartaric acid, malic acid, salicylic acid or phthalic acid, among others. Preferably, hydrochloric acid is used.

In a preferred embodiment of the invention, the tramadol is in the form of its hydrochloride salt, or tramadol hydrochloride. More preferably, it is found in the form of tramadol hydrochloride, in racemic form.

The concentration of tramadol in the ophthalmic pharmaceutical composition of the invention is preferably comprised between 0.05% and 2%, more preferably comprised between 0.075% and 1.5%, and even more preferably in a concentration of approximately of 0.1% (w/v) to 1.0% (w/v), expressed as equivalent concentration of tramadol hydrochloride.

Throughout the present description, the concentrations of tramadol in the ophthalmic composition of the invention always relate to the equivalent concentration of tramadol hydrochloride, irrespective of whether the tramadol is used in the form of free base or in the form of another salt. Thus, for example, a concentration of tramadol of 1% expressed as equivalent concentration of tramadol hydrochloride corresponds to a concentration of 0.878% of tramadol as free base, or a concentration of 1.079% of tramadol acetate, as the person skilled in the art already knows how to calculate, depending on the molecular weight of said substances, according to the equivalent quantities containing the same quantity of tramadol.

In a preferred embodiment of the invention, the concentration of tramadol is comprised between 0.05% and 0.2%, more preferably comprised between 0.075% and 0.14% and even more preferably is of approximately 0.1%, expressed as equivalent concentration of tramadol hydrochloride.

In another preferred embodiment of the invention, the concentration of tramadol is comprised between 0.25% and 1%, more preferably comprised between 0.40% and 0.65%, and even more preferably it is of approximately 0.5%, expressed as equivalent concentration of tramadol hydrochloride.

In another preferred embodiment of the invention, the concentration of tramadol is comprised between 0.5% and 2%, more preferably comprised between 0.75% and 1.35%, and even more preferably it is of approximately 1%, expressed as equivalent concentration of tramadol hydrochloride.

Compositions

In a preferred embodiment, the aqueous ophthalmic pharmaceutical composition comprises:
a) ibuprofen, or a pharmaceutically acceptable salt thereof, in a concentration comprised between 0.05% and 0.2%, preferably comprised between 0.075% and 0.14%, and more preferably in a concentration of approximately 0.1%; and
b) tramadol or a pharmaceutically acceptable salt thereof, in a concentration, expressed as equivalent concentration of tramadol hydrochloride, comprised between 0.05% and 0.2%, preferably comprised between 0.075% and 0.14% and more preferably in a concentration of approximately 0.1%.

In another preferred embodiment of the invention, the aqueous ophthalmic pharmaceutical composition comprises:
a) ibuprofen or a pharmaceutically acceptable salt thereof, in a concentration comprised between 0.05% and 0.2%, preferably comprised between 0.075% and 0.14%, and more preferably in a concentration of approximately 0.1%; and
b) tramadol or a pharmaceutically acceptable salt thereof, in a concentration, expressed as equivalent concentration of tramadol hydrochloride, comprised between 0.25% and 1%, preferably comprised between 0.40% and 0.65%, and more preferably in a concentration of approximately 0.5%.

In another preferred embodiment of the invention, the aqueous ophthalmic pharmaceutical composition comprises:
a) ibuprofen or a pharmaceutically acceptable salt thereof, in a concentration comprised between 0.05% and 0.2%, preferably comprised between 0.075% and 0.14%, and more preferably in a concentration of approximately 0.1%; and
b) tramadol or a pharmaceutically acceptable salt thereof, in a concentration, expressed as equivalent concentration of tramadol hydrochloride, comprised between 0.5% and 2%, preferably comprised between 0.75% and 1.35%, and more preferably in a concentration of approximately 1%.

In a particularly preferred embodiment of the invention, the aqueous ophthalmic pharmaceutical composition comprises:
a) ibuprofen, or a pharmaceutically acceptable salt thereof, in a concentration of approximately 0.1% (w/v); and
b) tramadol, or a pharmaceutically acceptable salt thereof, in a concentration of approximately 0.1% (w/v), expressed as equivalent concentration of tramadol hydrochloride.

In another particularly preferred embodiment of the invention, the aqueous ophthalmic pharmaceutical composition comprises:
a) ibuprofen, or a pharmaceutically acceptable salt thereof, in a concentration of approximately 0.1% (w/v); and
b) tramadol, or a pharmaceutically acceptable salt thereof, in a concentration of approximately 0.5% (w/v), expressed as equivalent concentration of tramadol hydrochloride.

In another particularly preferred embodiment of the invention, the aqueous ophthalmic pharmaceutical composition comprises:
a) ibuprofen, or a pharmaceutically acceptable salt thereof, in a concentration of approximately 0.1% (w/v); and
b) tramadol, or a pharmaceutically acceptable salt thereof, in a concentration of approximately 1.0% (w/v), expressed as equivalent concentration of tramadol hydrochloride.

In the compositions of the invention, the tramadol is preferably in the form of tramadol hydrochloride, more preferably as tramadol hydrochloride in racemic form.

Likewise, the ibuprofen is preferably in the form of salt with arginine, as defined above.

The ophthalmic pharmaceutical composition according to the present invention is defined as a composition designed for its local application in the eye or adjacent areas, for example, in the eyelids.

Typically, the ophthalmic composition according to the present invention is an aqueous composition.

The general characteristics of said ophthalmic compositions are well known for a person skilled in the art. Thus, for example, in the chapter "*Ophthalmic Preparations*", which corresponds to chapter 43 of the recognised manual of pharmaceutical technology "*Remington The Science and Practice of Pharmacy*", 20th edition, Lippincott, Williams & Wilkins, Philadelphia, 2000 [ISBN: 0-683-306472], the characteristics, formulation, mode of use and form of preparation of said compositions are described in detail.

The ophthalmic composition according to the present invention is topically administered on the eye surface, for example, in the form of drops by spraying. Alternatively, it can also be administered by subconjunctival injection or retrobulbar injection, as described in the aforementioned chapter "*Ophthalmic Preparations*".

Preferably, the composition of the invention is topically administered on the eye surface, including both direct administration on said surface and its deposit on the edges of the eyelids, as is already known by the person skilled in the art and as described in the aforementioned chapter. For example, the composition can be applied by a dropper, being instilled in the lower conjunctival sac, which is accessed by gently pulling the lower eyelid downwards forming a sac where the drop is deposited.

Preferably, the ophthalmic composition according to the present invention is an aqueous formulation which may be in the form of solution or suspension. In the ophthalmic solution all the ingredients are completely dissolved in the aqueous medium, whilst in the ophthalmic suspension, it is a dispersion in the aqueous vehicle of finely divided particles of the drug, relatively insoluble.

Preferably, the ophthalmic composition according to the present invention is in the form of solution.

The ophthalmic composition of the invention may optionally contain other additional ingredients.

As is known for the person skilled in the art, ophthalmic compositions preferably adjust to certain values of pH and osmolarity, in general close to the physiological values, with a view to minimizing the pain and discomfort in the eye area derived from their application.

The composition according to the present invention has a pH preferably comprised between 7.0 and 8.0, more preferably comprised between 7.3 and 7.7, and more preferably of approximately 7.5.

Thus, the composition optionally contains an agent to regulate the pH which is ophthalmically acceptable. Said pH regulating agents are well-known for a person skilled in the art and include, without limitation, acids such as hydrochloric acid, acetic acid or citric acid; and bases such as sodium hydroxide, sodium phosphate or sodium citrate. A buffering system can also be used which is acceptable for its ophthalmic application, to regulate the pH in the required values, which are also well known for a person skilled in the art, for example acetate buffer, citrate buffer, phosphate buffer, borate buffer or bicarbonate buffer or their mixtures.

The osmolarity of the composition must also adapt to the tonicity characteristics of the eye, to avoid discomfort in its application, so that it is preferably isotonic with respect to the eye, or slightly hypertonic or hypotonic.

The composition according to the present invention preferably has an osmolarity comprised between 280 mOsm/Kg and 350 mOsm/Kg, more preferably comprised between 290 mOsm/Kg and 340 mOsm/Kg, even more preferably comprised between 300 mOsm/Kg and 320 mOsm/Kg, and even more preferably of approximately 310 mOsm/Kg.

Thus, the composition optionally comprises an agent to regulate the osmolarity, or isotonizing agent, which is chosen, for example, among sodium chloride, potassium chloride, sodium sulfate, potassium nitrate, mannitol, glycerol, sorbitol, glucose and sucrose, and their mixtures. Preferably, the isotonizing agent is sodium chloride.

In a preferred embodiment of the invention, the composition contains sodium chloride as isotonizing agent in a proportion comprised between 0.5% and 1.5%, more preferably comprised between 0.75% and 1.25%.

Optionally, the composition of the invention contains an opthalmologically acceptable preservative ingredient, especially when the composition is disposed in typical multi-dose containers, to avoid the contamination of the composition once the container has been opened. In general, the presence of a preservative is not necessary when single-dose containers or multi-dose containers which maintain their content sterile are used.

Among the preservatives suitable for being used in the ophthalmic composition according to the present invention are, for example, the compounds of quaternary ammonium such as benzalkonium chloride, benzethonium chloride or cetylpyridinium chloride; the organomercuric compounds such phenylmercuric nitrate, phenylmercuric acetate, phenylmercuric borate or thimerosal; parabens, such as methylparaben or propylparaben; alcohols or substituted phenols, such as chlorobutanol, phenethyl alcohol, or benzyl alcohol; or others such as chlorhexidine, sorbic acid, potassium sorbate, sodium benzoate, or sodium propionate; or their mixtures. A preferred preservative is benzalkonium chloride.

Optionally, the composition of the invention contains a viscosizing agent, which has the function of increasing the viscosity of the composition, thereby managing to increase the retention time of the active principles in the eye, which in turn may favour its absorption. The viscosizing agent, on the other hand, also possibly has the effect of decreasing the sedimentation of particles in suspension, for the compositions in the form of suspension.

Among the viscosizing agents suitable for being used in the compositions of the invention are, for example, sodium carboxymethylcellulose, hydroxypropyl cellulose, hydroxylmethyl cellulose, hydroxyethyl cellulose, hydroxypropyl methylcellulose, methylcellulose, carbomers, polyvinylpyrrolidone, polyvinyl alcohol, polyoxyethylene, a polycarbophil, hyaluronic acid or its sodium salt, or their mixtures.

Optionally, the composition of the invention comprises a chelating agent, for example, sodium citrate or edetate salts, such as edetate disodium, edetate calcium disodium, edetate trisodium, or edetate dipotassium, or their mixtures.

Optionally, the composition of the invention comprises an antioxidant. Among the antioxidants suitable for being used in the composition according to the present invention are, for example, sodium bisulfite, ascorbic acid or acethylcisteine, or their mixtures.

Likewise, optionally, the composition of the invention comprises a surfactant whose function is, for example, that of increasing the solubility of active principles, as well as favouring the contact thereof with the eye surface on decreasing the surface tension of the liquid and favouring its penetration.

Among the surfactants suitable for being used in the composition of the invention are, for example, fatty esters of sorbitan polyoxyethylene (polysorbates), alkylphenol ethoxylates, ethylene glycol-propylene glycol block copolymers, lecithins or phospholipids.

Reference is made here to the recognised manual of excipients of pharmaceutical use, the "*Handbook of Pharmaceutical Excipients*" by Rowe R C, Sheskey P J and Quinn M E, sixth edition, 2009, where it is possible to find the definitions and characteristics for the different ingredients mentioned.

Therapeutic Indications

An object of the present invention is the use of a combination of ibuprofen, or a pharmaceutically acceptable salt thereof, and tramadol, or a pharmaceutically acceptable salt thereof, for the preparation of an ophthalmic pharmaceutical composition for the treatment of ocular inflammation and/or pain.

Alternatively, said object may be formulated as an ophthalmic pharmaceutical composition comprising ibuprofen, or a pharmaceutically acceptable salt thereof, and tramadol or a pharmaceutically acceptable salt thereof, for its use in the treatment of ocular inflammation and/or pain.

Preferably, the ophthalmic pharmaceutical composition is the composition of the invention.

Thus, part of the object of the invention is also the use of the composition of the invention for the preparation of a medicine for the treatment of ocular inflammation and/or pain.

In the framework of the present invention, the term treatment includes the treatment with therapeutic purpose, i.e. aimed at the elimination, reduction, improvement or relief of symptoms when they have already manifested themselves, and also includes the treatment with preventive or prophylactic purpose, i.e. aimed at preventing or delaying the appearance of the inflammation and/or ocular pain, or reducing its incidence.

The treatment according to the use of the present invention is indicated to be applied to any mammal animal which requires said treatment, preferably human beings.

Likewise, the ocular pain and/or inflammation according to the object of the present invention is understood in a broad sense, including both actual eye disorders, including all its parts, among them iris, crystalline lens, cornea, conjunctiva, sclera, choroid, retina, optic disc or vitreous humour; as well as in the surrounding areas, for example, the eyelids.

On the other hand, the aetiology of said pain or inflammation can be diverse, for example, as a response to traumatisms or eye surgery, or due to infectious processes, allergies, immunological reactions, or due to other causes, all of them being included in the field of the present invention.

Thus, the use which forms part of the present invention relates to the treatment of ocular inflammation and/or pain associated to various diseases or pathological states, for example, in non-limiting form, the following:

post-surgical states after eye surgery;
inflammatory states of diverse origin and localization, such as allergic conjunctivitis, viral conjunctivitis, bacterial conjunctivitis, blepharitis, uveitis, iridocyclitis, intermediate uveitis, chorioretinitis, scleritis, episcleritis, retinitis, or keratitis, among others;
dry eye syndrome;
eye lesion due to traumatism, burn, radiation, introduction of foreign body, or contact with chemical agents; or
use of contact lenses.

Within the framework of the present invention, the eye surgery includes any surgical technique performed in the eye, including, for example, cataract surgery, corneal transplant, occuloplasty, or any other refractive surgery technique. For its part, refractive surgery includes techniques such as radial keratotomy (RK), astigmatic keratotomy (AK), photorefractive keratectomy (PRK), or Laser In-Situ Keratomileusis (LASIK), all included in the field of the present invention. It also includes within the inflammatory and pain effects caused by eye surgery, in particular, macular edema after cataract surgery and photophobia after eye surgery, especially photophobia after refractive surgery.

In a particularly preferred embodiment, the use according to the present invention relates to the treatment of ocular inflammation and/or pain associated to post-surgical states after eye surgery.

In an even more preferred embodiment, the use according to the present invention relates to the treatment of ocular inflammation and/or pain associated to post-surgical states after cataract surgery, radial keratotomy (RK), photorefractive keratectomy (PRK), or Laser In-Situ Keratomileusis (LASIK), including macular edema after cataract surgery and photophobia after radial keratotomy (RK), and photophobia after photorefractive keratectomy (PRK).

The authors of the invention have verified that the ophthalmic compositions developed are surprisingly effective in the treatment of pain and ocular inflammation, and they are substantially free form adverse effects.

Thus, for example, the ocular analgesic effect of the composition of the invention was tested in an experimental model in mice, based on the inhibition of ocular pain induced by capsaicin, as described in the article González et al. *Reduction of capsaicin-induced ocular pain and neurogenic inflammation by calcium antagonists*. Invest. Ophthalmol. Vis. Sci., 1993, 34 (12), p 3329-35. The compositions of the invention, with the combination of ibuprofen and tramadol, showed a high efficiency in said model, without observing appreciable adverse effects.

Preparation of the Composition of the Invention

The aqueous composition for ophthalmic use according to the present invention is prepared using habitual processes, which are well known for the person skilled in the art, as described, for example, in the chapter "*Ophthalmic Formulations*" of the manual "*Remington The Science and Practice of Pharmacy*", mentioned above.

Thus, one of the requirements that the ophthalmic compositions must comply with is that they must be sterile. Different techniques can be used for the sterilization of the ophthalmic compositions of the invention, all well known by persons skilled in the art, for example, with high-pressure steam at 121° C. (in an autoclave), by sterilizing filtration, sterilization with ethylene oxide, or by radiation.

Preferably, the ophthalmic composition of the invention is sterilized by sterilizing filtration and/or with high-pressure steam at 121° C.

The aqueous composition of the invention can be prepared with purified water, according to the characteristics specified in the Spanish Royal Pharmacopoeia, second edition, or with water for injection.

Thus, the composition for ophthalmic use according to the present invention can be prepared, for example, according to a process comprising the dissolution or dispersion in purified water/water for injection of the active ingredients ibuprofen, or a salt thereof, and tramadol, or a salt thereof, together with other possible optional ingredients, such as an isotonizing agent, a preservative agent, a viscosizing agent, among others, as described above, or a combination thereof.

The pH of the composition adjusts to a value comprised between 7.0 and 8.0, an aqueous solution of an acid and/or a base being added if necessary.

Finally, if necessary, additional purified water/water for injection is added until the required final volume, and it is also verified that the value of the osmolarity is comprised between the recommended values, i.e. between 280 mOsm/Kg and 350 mOsm/Kg.

The solution obtained can be sterilized, for example, by sterilizing filtration.

Finally, the resulting solution can be dosed in multi-dose or single-dose containers, suitable for ophthalmic administration as are well known by a person skilled in the art in pharmaceutical technology. Optionally, said packages that contain the composition of the invention are sterilized in an autoclave, for example, by treatment at 121° C. during approximately 20 minutes.

The composition of the present invention can be prepared according to processes that do not require the use of inert atmosphere, so that, optionally, it is possible to use nitrogen or another inert gas exclusively to push the solution during the sterilizing filtration process.

Below, several examples are provided as an illustrative, though non-limiting, example of the invention.

EXAMPLES

Example 1

Eyedrops at 0.1% Ibuprofen and 0.1% Tramadol Hydrochloride

An aqueous solution was prepared using the proportions detailed in the following table:

| Ingredient | Quantity % (w/v) |
|---|---|
| Ibuprofen | 0.100 |
| Tramadol HCl | 0.100 |
| L-Arginine | 0.089 |
| NaCl | 0.990 |
| Purified water | q.s. 100 ml |

One part of the purified water, in a quantity of approximately 75% of the total was placed in a reactor. Then, under constant stirring, L-arginine, tramadol hydrochloride, ibuprofen and sodium chloride were consecutively added until total dissolution.

The pH was then determined, which had a value of 7.57, and the remainder of the purified water was added flushing until the final volume. The solution thus obtained was sterilized by filtration through a 0.22 micron filter.

The solution had an osmolarity of 313 mOsm.

Example 2

Eyedrops at 0.1% Ibuprofen and 0.5% Tramadol Hydrochloride

An aqueous solution was prepared using the proportions detailed in the following table:

| Ingredient | Quantity % (w/v) |
|---|---|
| Ibuprofen | 0.100 |
| Tramadol HCl | 0.500 |
| L-Arginine | 0.089 |
| NaCl | 0.920 |
| 0.01M NaOH | 1.732 |
| Purified water | q.s. 100 ml |

For the preparation of this composition, a process similar to that described in Example 1 was described so that ibuprofen, tramadol HCl, L-arginine and NaCl were dissolved in purified water. The pH was determined and it was adjusted to a value of 7.54 with a 0.01M NaOH solution, and purified water was added flushing until the final volume. The final osmolarity of the solution obtained was of 312 mOsm.

Example 3

Eyedrops at 0.1% Ibuprofen and 1% Tramadol Hydrochloride

An aqueous solution was prepared using the proportions detailed in the following table:

| Ingredient | Quantity % (w/v) |
|---|---|
| Ibuprofen | 0.100 |
| Tramadol HCl | 1.000 |
| L-Arginine | 0.089 |
| NaCl | 0.790 |
| 0.01M NaOH | 6.114 |
| Purified water | q.s. 100 ml |

For the preparation of this composition, a process similar to that followed in the previous examples was followed. In this case the pH value was also adjusted with a 0.01M NaOH solution until a value of 7.55. The final osmolarity of the solution obtained was of 306 mOsm.

The invention claimed is:

1. An aqueous ophthalmic pharmaceutical composition comprising:
   a) ibuprofen arginate in a concentration of between 0.075% (w/v) and 0.14% (w/v), expressed as equivalent concentration of ibuprofen, wherein the molar ratio between ibuprofen:arginine is between 1.2:1 and 1:1.2; and
   b) tramadol, or a pharmaceutically acceptable salt thereof, in a concentration, expressed as equivalent concentration of tramadol hydrochloride, of between 0.25% (w/v) and 1% (w/v).

2. The composition according to claim 1, characterised in that it comprises:

a) ibuprofen arginate in a concentration of 0.1% (w/v), expressed as an equivalent concentration of ibuprofen; and
b) tramadol, or a pharmaceutically acceptable salt thereof, in a concentration of 0.5% (w/v), expressed as equivalent concentration of tramadol hydrochloride.

3. The composition according to claim 1, characterised in that it comprises:
a) ibuprofen arginate in a concentration of 0.1% (w/v), expressed as an equivalent concentration of ibuprofen; and
b) tramadol, or a pharmaceutically acceptable salt thereof, in a concentration of the 1.0% (w/v), expressed as equivalent concentration of tramadol hydrochloride.

4. The composition according to claim 1, characterised in that the molar ratio between ibuprofen: arginine is between 1:1.05 and 1:1.1.

5. The composition according claim 1, characterised in that the tramadol is in the form of tramadol hydrochloride.

6. The composition according to claim 1, characterised in that it further comprises sodium chloride as an isotonizing agent.

7. The composition according to claim 6, characterised in that it comprises sodium chloride in a proportion comprised between 0.75% (w/v) and 1.25% (w/v).

8. The composition according to claim 1, characterised in that it has a pH of between 7.0 and 8.0 and an osmolarity of between 280 mOsm/Kg and 350 mOsm/Kg.

9. The composition according to claim 1 characterised in that it further comprises hydroxypropyl methylcellulose as a viscosizing agent.

10. A method of treating ocular inflammation and/or pain with the aqueous ophthalmic pharmaceutical composition of claim 1 comprising topically administering the composition to an affected eye, wherein the ocular inflammation and/or pain is mydriasis.

11. An aqueous ophthalmic pharmaceutical composition consisting of:
a) ibuprofen arginate in a concentration of 0.1% (w/v), expressed as equivalent concentration of ibuprofen, wherein the molar ratio between ibuprofen:arginine is between 1.2:1 and 1:1.2; and
b) tramadol, or a pharmaceutically acceptable salt thereof, in a concentration, expressed as equivalent concentration of tramadol hydrochloride, of 0.5% (w/v) as the active ingredients.

* * * * *